(12) United States Patent
Hiraoka et al.

(10) Patent No.: US 7,259,149 B2
(45) Date of Patent: Aug. 21, 2007

(54) METHODS FOR TREATING OR PREVENTING ANGIOGENESIS-DEPENDENT SYMPTOMS

(75) Inventors: Kazuya Hiraoka, Osaka (JP); Seiji Yamamoto, Suita (JP); Yasufumi Kaneda, Minoh (JP); Ryuichi Morishita, Osaka (JP); Toshio Ogihara, Minoh (JP)

(73) Assignee: AnGes MG, Inc., Osaka (JP)

( * ) Notice: Subject to any disclaimer, the term of this patent is extended or adjusted under 35 U.S.C. 154(b) by 0 days.

(21) Appl. No.: 10/536,274

(22) PCT Filed: Dec. 2, 2003

(86) PCT No.: PCT/JP03/15400

§ 371 (c)(1),
(2), (4) Date: Nov. 14, 2005

(87) PCT Pub. No.: WO2004/050126

PCT Pub. Date: Jun. 17, 2004

(65) Prior Publication Data

US 2006/0135452 A1 Jun. 22, 2006

Related U.S. Application Data

(60) Provisional application No. 60/430,478, filed on Dec. 2, 2002.

(51) Int. Cl.
*A61K 48/00* (2006.01)
*C12N 15/63* (2006.01)

(52) U.S. Cl. .................... 514/44; 435/320.1
(58) Field of Classification Search ............ 514/44; 435/320.1
See application file for complete search history.

(56) References Cited

U.S. PATENT DOCUMENTS

| | | | |
|---|---|---|---|
| 2002/0137707 A1 | 9/2002 | Budker et al. | |
| 2003/0171287 A1* | 9/2003 | Morishita et al. | 514/12 |
| 2004/0087535 A1 | 5/2004 | Morishita et al. | |

FOREIGN PATENT DOCUMENTS

WO  WO97/40679 A1  11/1997

OTHER PUBLICATIONS

Taniyama et al. Gene Ther. 8:181-189; 2001.*
Lubiatowski et al. Plast. Reconstr. Surg. 109:1986-1993; 2002.*
Grim et al. JAMA 263; 1990; Abstract.*
Niidome et al. Gene Ther. 9:1647-1652; 2002.*
Database; BIOSIS Accession No. PREV200200261758; Mar. 2002, and: Taniyama et al.; "Development of safe and efficient novel nonviral gene transfer using ultrasound: Enhancement of transfection efficiency of naked plasmid DNA in skeletal muscle"; *Gene Therapy* 9(6):372-380 (Mar. 2002).
Database, BIOSIS Accession No. PREV199800207109; Mar. 31, 1998; and: Baumgartner, Iris et al.; "Constitutive expression of phVEGF165 after intramuscular gene transfer promotes colleteral vessel development in patients with critical limb ischemia"; *Circulation* 97(12):1114-1123 (Mar. 31, 1998).
Database; BIOSIS Accession No. PREV200100114748; Feb. 2001; and: Taniyama, Y. et al.; "Therapeutic angiogenesis induced by human hepatocyte growth factor gene in rat and rabbit hindlimb ischemia models: Preclinical study for treatment of peripheral arterial disease"; *Gene Therapy* 8(3):181-189 (Feb. 2001).
Database; BIOSIS Accession No. PREV200200358126; May 2002; and: Comerota, Anthony J. et al.; "Naked plasmid DNA encoding fibroblast growth factor type 1 for the treatment of end-stage unreconstructible lower extremity ischemia: Preliminary results of a phase I trial"; *Journal of Vascular Surgery* 35(5):930-935 (May 2002).
Database; BIOSIS Accession No. PREV200400009718; Nov. 25, 2003; and: Kazuya, Hiraoka et al.; "Enhanced therapeutic angiogenesis by cotransfection of prostacyclin synthase gene or optimization of intramuscular injection of naked plasmid DNA"; *Circulation* 108(21):2689-2696 (Nov. 25, 2003).
Feeley, Brian T., et al.; "Optimization of ex vivo pressure mediated delivery of antisense oligodeoxynulceotides to ICAM-1 reduced reperfusion injury in rat cardiac allografts," *Transplantation*; Mar. 27, 2000; pp. 1067-1074; 69:6.
Feeley, Brian T., et al.; Database EMBASE; Accession No. EMB-2000145210; "Optimization of ex vivo pressure mediated delivery of antisense oligodeoxynulceotides to ICAM-1 reduces reperfusion injury in rat cardiac allografts," *Transplantation*; Mar. 27, 2000.

* cited by examiner

*Primary Examiner*—Anne M. Wehbe'
*Assistant Examiner*—Fereydoun G. Sajjadi
(74) *Attorney, Agent, or Firm*—Townsend and Townsend and Crew LLP

(57) ABSTRACT

A method for enhancing the transfection efficiency of naked plasmid DNA in treating and/or preventing angiogenesis-dependent symptoms is provided by the present inventions. According to the present method, a suitable naked plasmid DNA is subjected for intramuscular injection under increased pressure inside the muscle or hyperbaric oxygen. Angiogenesis-dependent symptoms, including wounds, inflammatory diseases, critical limb ischemia, ischemia heart diseases, cerebral infarction, diabetic neuropathy, spinal canal stenosis, etc., may be treated by the present methods.

4 Claims, 8 Drawing Sheets

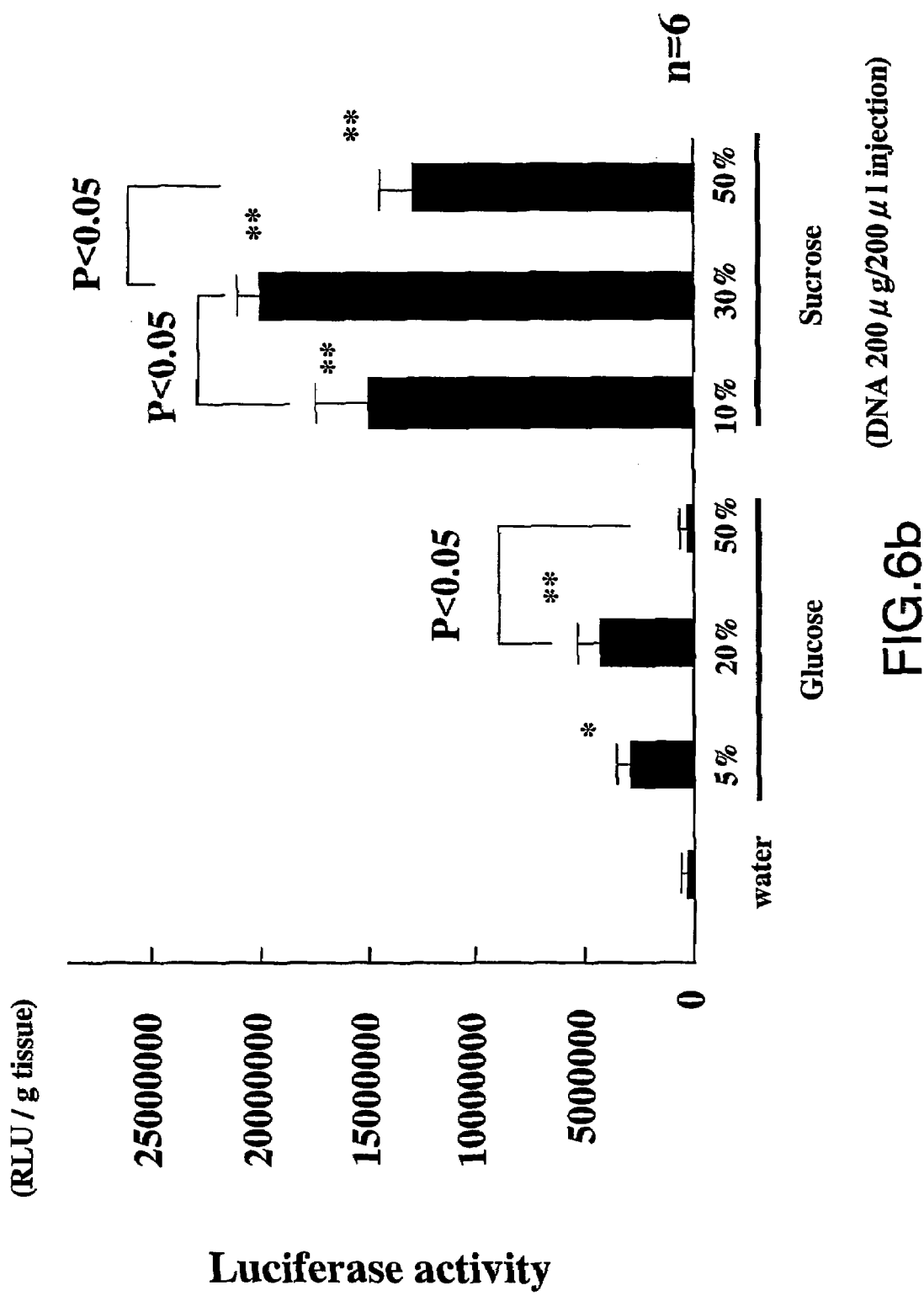

METHODS FOR TREATING OR PREVENTING ANGIOGENESIS-DEPENDENT SYMPTOMS

TECHNICAL FIELD

The present invention relates to methods for treating and/or preventing angiogenesis-dependent symptoms by administering an intramuscular injection of a naked plasmid DNA under specific conditions, such as increased pressure inside the muscle or hyperbaric oxygen.

BACKGROUND ART

Recent progress in molecular biology has led to the development of gene therapy as a new treatment strategy for cardiovascular diseases. Targeted diseases range from single gene deficiency diseases to more complex diseases in adults, such as peripheral arterial diseases. For example, critical limb ischemia is estimated to develop in 500 to 1000 per million individuals in one year ("Second European Consensus Document on Chronic Critical Leg Ischemia.", Circulation 84(4 Suppl.) IV 1-26 (1991)). In patients with critical limb ischemia, amputation, despite its associated morbidity, mortality and functional implications, is often recommended as a solution against disabling symptoms (M. R. Tyrrell et al., Br. J. Surg. 80: 177-180 (1993); M. Eneroth et al., Int. Orthop. 16: 383-387 (1992)). There exists no optimal medical therapy for critical limb ischemia (Circulation 84(4 Suppl.): IV 1-26 (1991)).

Recently, the efficacy of therapeutic angiogenesis by gene transfer of vascular endothelial growth factor (VEGF) has been reported to be effective for human patients with critical limb ischemia (I. Baumgartner et al., Circulation 97: 1114-1123 (1998); J. M. Isner et al., J. Vasc. Surg. 28: 964-973 (1998); I. Baumgartner et al., Ann. Intern. Med. 132: 880-884 (2000)) and myocardial ischemia (D. W. Losordo et al., Circulation 98: 2800-2804 (1998); P. R. Vale et al., Circulation 102: 965-974 (2000); T. K. Rosengart et al., Circulation 100: 468-474 (1999); T. K. Rosengart et al., Ann. Surg. 230: 466-470 (1999)). In addition to VEGF, gene transfer of other angiogenic growth factors, including fibroblast growth factor (FGF), hepatocyte growth factor (HGF) and hypoxia-inducible factor (HIF), has also been reported to stimulate collateral formation (Y. Taniyama et al., Gene Ther. 8: 181-189 (2000); H. Tabata et al., Cardiovasc. Res. 35: 470-479 (1997); H. Ueno et al., Arterioscler. Thromb. Vasc. Biol. 17: 2453-2460 (1997); K. A. Vincent et al., Circulation 102: 2255-2261 (2000); F. J. Giordano et al., Nat. Med. 2: 534-539 (1996); M. Aoki et al., Gene Ther. 7: 417-427 (2000); H. Ueda et al., Ann. Thorac. Surg. 67: 1726-1731 (1999); E. R. Schwarz et al., J. Am. Coll. Cardiol. 35: 1323-1330 (2000)).

The feasibility of gene therapy using angiogenic growth factors to treat peripheral arterial disease seems to be superior to recombinant protein therapy. For example, through gene therapy, one can potentially maintain an optimally high and local concentration over time. Thus, in the case of therapeutic angiogenesis, to avoid side effects, it may be desirable to deliver a lower dose of protein through an actively expressed transgene in the artery over a period of several days or more, rather than administering a single or multiple bolus doses of recombinant protein. Interestingly, most successful clinical trials treating peripheral arterial diseases using angiogenic growth factors have involved intramuscular transfection of naked plasmid DNA (I. Baumgartner et al., Circulation 97: 1114-1123 (1998); J. M. Isner et al., J. Vasc. Surg. 28: 964-973 (1998); I. Baumgartner et al., Ann. Intern. Med. 132: 880-884 (2000); D. W. Losordo et al., Circulation 98: 2800-2804 (1998); P. R. Vale et al., Circulation 102: 965-974 (2000)). However, such in vivo gene transfer, by direct injection of "naked" plasmid DNA into skeletal muscle, has been known to be inefficient.

Therefore, more efficient methods for gene transfer are required in the art for therapeutic application. Thus, many investigators have been focusing on alternate methods, such as the adenoviral gene transfer method (H. Ueno et al. Arterioscler. Thromb. Vasc. Biol. 17: 2453-2460 (1997); F. J. Giordano et al., Nat. Med. 2: 534-539 (1996); D. F. Lazarous et al., Cardiovasc. Res. 44: 294-302 (1999); L. Y. Lee et al., Ann. Thorac. Surg. 69: 14-23 (2000); L. H. Gowdak et al., Circulation 102: 565-571 (2000); O. Varenne et al., Hum. Gene Ther. 10:1105-1115 (1999); E. Barr et al., Gene Ther. 1: 51-58 (1994)). Although adenoviral vectors are efficient (H. Ueno et al., Arterioscler. Thromb. Vasc. Biol. 17: 2453-2460 (1997); F. J. Giordano et al., Nat. Med. 2: 534-539 (1996); D. F. Lazarous et al., Cardiovasc. Res. 44: 294-302 (1999); L. Y. Lee et al., Ann. Thorac. Surg. 69: 14-23 (2000); L. H. Gowdak et al., Circulation 102: 565-571 (2000); O. Varenne et al., Hum. Gene Ther. 10:1105-1115 (1999); E. Barr et al., Gene Ther. 1: 51-58 (1994)), they have some theoretical disadvantages, such as induction of strong immunogenicity in the host (V. J. Dzau et al., Proc. Natl. Acad. Sci. USA 93: 11421-11425 (1996)). In addition to efficiency, safety is also an important issue for gene transfer methods. The infusion of adenovirus has recently been reported to cause deleterious side effects (E. Marshall, Science 286: 2244-2245 (1999)). Thus, in the interests of safety, it would be more desirable to make non-virus-mediated plasmid DNA more efficient to achieve an ideal treatment for peripheral arterial diseases. Such innovation in plasmid DNA-based gene transfer should provide methods with high transfection efficiency without severe side effects.

To increase the transfection efficiency of naked plasmid DNA, the present inventors previously tested the use of ultrasound and echo contrast microbubbles (Optison® (FS069); Molecular Biosystems). As a result, the inventors discovered that high transfection efficiency could be achieved by ultrasound-mediated plasmid DNA transfection using echo contrast microbubbles (Y. Taniyama et al., Circulation 105: 1233-1239 (2002); Y. Taniyama et al., Gene Therapy 9: 372-380 (2002)). Using ultrasound exposure in the presence of microbubble echo contrast agents, approximately 300-fold increment in transgene expression following naked DNA transfection was reported in in vitro experiments (A. Lawrie et al., Gene Ther. 9: 372-380 (2002)) In addition, the inventors confirmed the usefulness of ultrasound-mediated plasmid DNA transfection with Optison® into rat skeletal muscle as well as rat carotid artery (Y. Taniyama et al., Circulation 105: 1233-1239 (2002); Y. Taniyama et al., Gene Therapy 9: 372-380 (2002)). Due to the appearance of transient holes in the cell membrane through the spreading of the bubbles, this method increased the transfection efficiency.

DISCLOSURE OF THE INVENTION

Although clinical trials of stimulation of angiogenesis by transfection of angiogenic growth factors via intramuscular injection of naked plasmid DNA have been successful, there still are unresolved problems in human gene therapy, including low transfection efficiency and safety. From this viewpoint, methods that achieve higher transfection efficiency for naked plasmid DNA are desired in the art.

The object of the present invention is to provide methods for treating and/or preventing angiogenesis-dependent symptoms by administering naked plasmid DNA with high transfection efficiency. As described above, the present inventors previously investigated the use of ultrasound-mediated plasmid DNA transfection using echo contrast microbubbles. Based on the efficient transfection achieved by this method, the inventors thought that destabilizes the cellular membrane through high osmotic pressure might increase the transfection efficiency of the naked plasmid DNA method. Therefore, the present inventors examined various agents and pressures on the injected site for their effect on the transfection efficiency of naked plasmid DNA in vivo.

First, the present inventors examined the effects of injection volume on the efficiency of naked plasmid DNA transfection into the cells of the skeletal muscles. Luciferase plasmid DNA dissolved in various volumes of solvent was subjected for intramuscular injection into the rat hindlimb. According to the present data, the transfection efficiency of naked plasmid DNA seemed to be determined by the amounts of plasmid DNA as well as the injection volume of solution injected into the skeletal muscle, a phenomenon seemingly caused by the increase in pressure on the cellular surface. However, applying pressure to the site of injection from outside the body (using the manchette of a sphygmomanometer on the hindlimb, for example) did not increase the transfection efficiency. In contrast, injection of phosphate-buffered saline (PBS) solution 30 minutes after plasmid DNA injection increased the transfection efficiency of the plasmid DNA, whereas additional injection of PBS solution after 5 hours did not. These data clearly demonstrate that high pressure inside the muscle is critical for increasing transfection efficiency.

Furthermore, the present inventors discovered that the intramuscular injection of plasmid DNA in combination with hyperbaric oxygen (HBO) therapy enhances the transfection efficiency of naked plasmid DNA. Moreover, the influence of the kind of solutions for dissolving the plasmid DNA was also determined. High transfection efficiency was achieved by saline as well as PBS, but not with water. Interestingly, sucrose solution rather than glucose solution resulted in high luciferase activity.

Overall, the transfection efficiency of intramuscular injection of plasmid DNA was enhanced by increases in the injection volume and osmotic pressure. Gene therapy using naked plasmid DNA of angiogenic growth factors with HBO therapy may provide a safe clinical gene therapy for arterial diseases without viral vector.

Thus, the present invention provides methods for treating and/or preventing angiogenesis-dependent symptoms by administering naked plasmid DNA under increased pressure at the administration site or in combination with HBO therapy. More specifically, the present invention provides:

(1) a method for treating or preventing an angiogenesis-dependent symptom comprising the step of injecting a suitable naked plasmid DNA into a muscle under a condition wherein the pressure inside the muscle is increased;
(2) the method of (1), wherein the pressure inside the muscle is increased by adopting a large injection volume;
(3) the method of (1), wherein the pressure inside the muscle is increased by injecting PBS after plasmid DNA administration;
(4) the method of (1), wherein the naked plasmid DNA is diluted in saline, PBS, sucrose solution, or glucose solution;
(5) the method of (1), wherein the naked plasmid DNA encodes an angiogenic growth factor;
(6) the method of (5), wherein the angiogenic growth factor is selected from the group consisting of: hepatocyte growth factor (HGF); vascular endothelial growth factor (VEGF); fibroblast growth factor (FGF); and nitric oxide synthase, including macrophage derived nitric oxide synthase, inducible nitric oxide synthase, and brain derived nitric oxide synthase;
(7) the method of (1), wherein the angiogenesis-dependent symptom is selected from the group consisting of: wounds, including bedsore and skin ulcer; inflammatory diseases; critical limb ischemia; ischemia heart diseases, such as myocardial infarction, angina pectoris, and heart failure; cerebral infarction; diabetic neuropathy; and spinal canal stenosis;
(8) a method for treating or preventing angiogenesis-dependent symptom through intramuscular injection of naked plasmid DNA in combination with hyperbaric oxygen (HBO) therapy;
(9) the method of (8), wherein the HBO therapy is conducted by exposure of 100% oxygen;
(10) the method of (8), wherein the subject to be treated is subjected to the HBO therapy immediately after plasmid DNA administration;
(11) the method of (8), wherein the naked plasmid DNA is diluted in saline, PBS, sucrose solution, or glucose solution;
(12) the method of (8), wherein the naked plasmid DNA encodes an angiogenic growth factor;
(13) the method of (12), wherein the angiogenic growth factor is selected from the group consisting of: hepatocyte growth factor (HGF); vascular endothelial growth factor (VEGF); fibroblast growth factor (FGF); and nitric oxide synthase, including macrophage derived nitric oxide synthase, inducible nitric oxide synthase, and brain derived nitric oxide synthase; and
(14) the method of (8), wherein the angiogenesis-dependent symptom is selected from the group consisting of: wounds, including bedsore and skin ulcer; inflammatory diseases; critical limb ischemia; ischemia heart diseases, such as myocardial infarction, angina pectoris, and heart failure; cerebral infarction; diabetic neuropathy; and spinal canal stenosis.

BRIEF DESCRIPTION OF THE DRAWINGS

FIG. 6b depicts a graph showing the effects of glucose and sucrose concentration on the luciferase activity 2 days after transfection of naked plasmid DNA (200 μg) into the skeletal muscle. Intramuscular injection of luciferase plasmid DNA (200 μg) using glucose (5, 20 and 50%) or sucrose (10, 30 and 50%) comprising solutions (200 μl injection volume) was performed. Each group contained 6 animals. **$p<0.01$ vs. water.

BEST MODE FOR CARRYING OUT THE INVENTION

Figure 1:
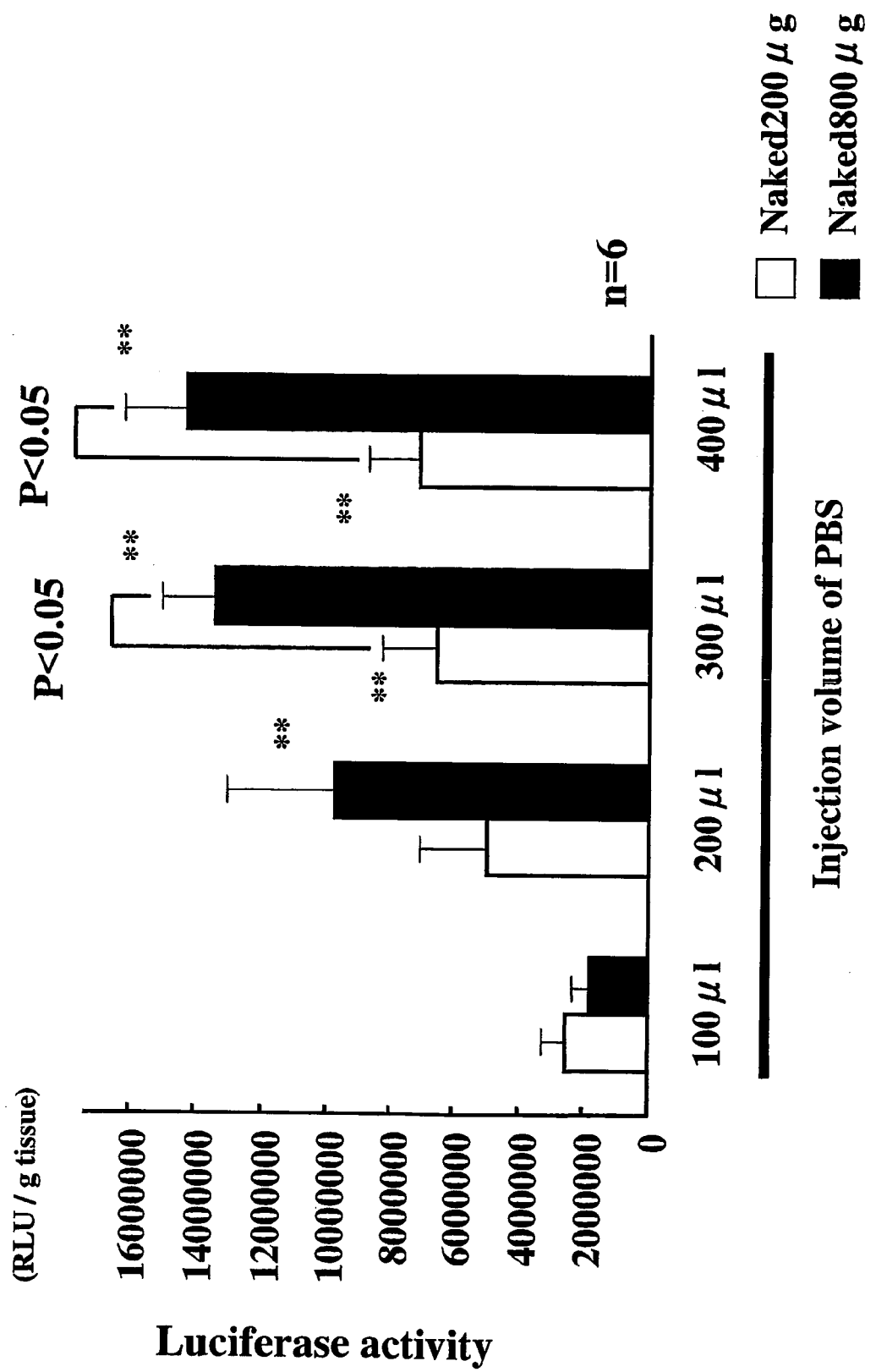
FIG. 1 depicts a graph showing the comparison of luciferase activities detected 2 days after transfection of naked plasmid DNA at various injection volumes into the skeletal muscle in vivo. Naked luciferase plasmid DNA (200 or 800 μg) diluted in 100, 200, 300 and 400 μl PBS were transfected into rats. Each group contained 6 animals. **$p<0.01$ vs. 100 μl.

The words "a", "an" and "the" as used herein mean "at least one" unless otherwise specifically indicated.

To find an optimal condition for plasmid DNA transfer into skeletal muscle, the present inventors modified the plasmid DNA gene transfer method. First, the inventors examined the influence of injection volume of plasmid DNA solution on the transfection efficiency. Next, the influence of the kind of solution to dissolve plasmid DNA was examined. Furthermore, the combined application of hyperbaric oxygen (HBO) therapy with plasmid DNA transfer was examined.

As a result, the transfection efficiency of naked plasmid DNA appeared to be increased by high pressure inside the muscle. Thus, the present invention provides a method for treating or preventing angiogenesis-dependent symptoms by intramuscular injection of a suitable naked plasmid DNA under a condition wherein the pressure inside the muscle is increased. The invention provides a method for alleviating an angiogenesis-dependent symptom, inhibiting development of the symptom, or suppressing the symptom in a subject.

According to the present invention, the phrase "angiogenesis-dependent symptoms" refers to symptoms of diseases that can be prevented, alleviated, improved or treated by angiogenesis. The symptoms that can be treated or prevented according to the present invention include: wounds, including bedsores and skin ulcers; inflammatory diseases; critical limb ischemia; ischemia heart diseases, such as myocardial infarction, angina pectoris and heart failure; cerebral infarction; diabetic neuropathy; and spinal canal stenosis.

Any plasmid DNA may be used for the present invention so long as the plasmid DNA contains a gene that encodes an angiogenic growth factor in an expressible manner upon introduction into the host. The gene encoding an angiogenic growth factor of the present invention is not limited in any way and includes those encoding proteins, polypeptides and parts thereof, so long as it has the ability to alleviate, improve or suppress the angiogenesis-dependent symptoms or prevents the development of the symptoms. Examples of preferred genes of the present invention include, but are not limited to, those encoding hepatocyte growth factor (HGF); vascular endothelial growth factor (VEGF); fibroblast growth factors (FGF), such as acidic FGF, basic FGF and FGF-4; nitric oxide synthases (NOS); VEGF-2; transforming growth factor (TGF)-α; TGF-β; platelet-derived (PD)-endothelial cell growth factor (ECGF); platelet-derived growth factor (PDGF); tumor necrosis factor (TNF)-α; insulin-like growth factor and antiopoietin-1.

The nucleotide sequence of a gene encoding HGF is described in the literature (Nature 342: 440 (1989); Japanese Patent No. 2577091; Biochem. Biophys. Res. Commun. 163: 967 (1989); Biochem. Biophys. Res. Commun. 172: 321 (1990)). Any of these disclosed sequences may be used as the angiogenic growth factor-encoding gene in the present invention.

Four subtypes are reported for the VEGF gene (VEGF121, VEGF165, VEGF189 and VEGF206; Science 219: 983 (1983); J. Clin. Invest. 84: 1470 (1989); Biochem. Biophys. Res. Commun. 161: 851 (1989)). Any one of them may be used as the angiogenic growth factor-encoding gene in the present invention. However, among the four, VEGF165 is known to possess the strongest biological activity, and thus is more preferred in the present invention.

Several isoforms of NOS have been isolated, including NOS isolated from: brain (nNOS; Bredt and Snyder, Proc. Natl. Acad. Sci. USA 87: 682-685 (1990)); endothelial cells (eNOS; Fostermann et al., Biochem. Pharmacol. 42: 1849-1857 (1991)); macrophages (iNOS; Hibbs et al., Science 235: 473 (1987); Stuehr et al., Proc. Natl. Acad. Sci. USA 88: 7773-7777 (1991)); hepatocytes (Knowles et al., Biochem. J. 279: 833-836 (1990)); vascular cells (Wood et al., Biochem. Biophys. Res. Commun. 170: 80-88 (1991)); and neutrophils (Yui et al., J. Biol. Chem. 266: 12544-12547 (1991); Yui et al., J. Biol. Chem. 266: 3369-3371 (1991)). In addition, NOS has been also isolated from other tissues (see, e.g., Hevel et al., J. Biol. Chem. 266: 22789-22791 (1991); Ohshima et al., Biochem. Biophys. Res. Commun. 183: 238-244 (1992); Hiki et al., J. Biochem. 111: 556-558 (1992); Evans et al., Proc. Natl. Acad. Sci. USA 89: 5361-5365 (1992); Sherman et al., Biochemistry 32: 11600-11605 (1993)). Thus, genes encoding the above-mentioned NOS derived from various organs and tissues can be used as the gene encoding angiogenic growth factor of the present invention. For example, the nucleotide sequence and amino acid sequence of human eNOS is publicly available through the GenBank database (GenBank Accession Nos. AF400594 and P29474, respectively; see also Janssens et al., J. Biol. Chem. 267(21): 14511-14522 (1992); Marsden et al., FEBS Lett. 307(3): 287-293 (1992)). In addition, isoforms are known to exist for eNOS (Fischman et al., Nat. Struct. Biol. 6(3): 233-242 (1999)); such isoforms are also included in the NOS of the present invention. Further sequence information of NOS that can be used in the present invention include those of mammalian calmodulin-dependent NOS (nNOS; U.S. Pat. No. 5,268,465), human inducible NOS (iNOS; U.S. Pat. No. 5,468,630) and bovine endothelial NOS (eNOS; U.S. Pat. No. 5,498,539).

Those skilled in the art can obtain cDNA that encodes an angiogenic growth factor by, for example, reverse transcriptase polymerase chain reaction (RT-PCR), using primers constructed from the publicly available sequence information for the above-mentioned genes (see, e.g., Molecular Cloning 2 nd ed., Cold Spring Harbor Laboratory Press (1989); PCR: a Practical Approach, IRL Press, Oxford (1991)) from sources comprising the angiogenic growth factor-encoding gene, which include cDNA libraries and genomic libraries of any mammalian species. However, in terms of immunogenicity, it is preferable to use genes from the same source as the animal to be treated with the gene.

The gene encoding an angiogenic growth factor used in the present invention is not limited to those described above. Rather, a gene is suitable for the present invention so long as it codes for a protein having angiogenic activity and includes: (1) a nucleotide sequence that hybridizes under stringent conditions to one of the above-described cDNA; and (2) a nucleotide sequence encoding a protein comprising the amino acid sequence encoded by the above-mentioned cDNA, in which one or more amino acids are substituted, deleted, added and/or inserted. Such nucleotides encoding mutant angiogenic growth factors can be readily obtained by site-directed mutagenesis (edit. Ausubel et al., Current Protocols in Molecular Biology, John Wiley & Sons, Section 8.1-8.5 (1987)); gene amplification methods such as PCR (edit. Ausubel et al., Current Protocols in Molecular Biology, John Wiley & Sons, Section 6.1-6.4 (1987); and general hybridization methods (J. Sambrook et al., Molecular Cloning 2 nd ed., Cold Spring Harbor Press, Section 9.47-9.58 (1989); edit. Ausubel et al., Current Protocols in Molecular Biology, John Wiley & Sons, Section 6.3-6.4 (1987)). Alternatively, the genes or fragments thereof may be chemically constructed based on their sequence information.

A stringent condition for hybridization normally includes a wash condition of "1×SSC, 37° C.". A more stringent condition would be a wash condition of "0.5×SSC, 0.1% SDS, 42° C.", and a much more stringent condition would be "0.1×SSC, 0.1% SDS 65° C.". The more stringent the condition, the higher the homology of the obtained polynucleotide to the probe sequence. However, the hybridization conditions mentioned above are merely examples, and it should be understood that those skilled in the art can select an appropriate condition for hybridization, taking the nucleotide sequence, concentration and length of the probe; reaction time; reaction temperature; concentration of the reagent; etc. into consideration.

The gene encoding an angiogenic growth factor of the present invention isolated by the above-mentioned hybridization techniques normally encodes a polypeptide that is highly homologous at the amino acid sequence level to the natural occurring angiogenic growth factor used as the probe. "Highly homologous" herein refers to an identity higher than 50%, preferably 65%, more preferably 75%, even more preferably 80%, much more preferably 90% and most preferably 95% or higher. Methods for determining sequence homology between polynucleotides are known in the art, and may be determined following the BLAST search algorithm (Karlin and Altschul, Proc. Natl. Acad. Sci. USA 90: 5873-5877 (1993)).

A mutation of proteins may occur in nature too. As mentioned above, various isoforms of respective angiogenic growth factors are known in the art. Such isoforms are also included in the angiogenic growth factor-encoding gene to be used in the present invention, so long as they retain the angiogenic activity of the native protein. It is well known that a protein modified by substitution, deletion, addition and/or insertion of one or more amino acid residues in the sequence of a protein can retain its original biological activity (G. Dalbadie-McFarland et al., Proc. Natl. Acad. Sci. USA 79: 6409-6413 (1982)).

To conserve the angiogenic activity of an angiogenic growth factor, it is preferable to mutate the amino acid residue into one that allows the properties of the amino acid side-chain to be conserved. The properties of amino acids are generally classified into: (1) Hydrophobic amino acids (alanine, isoleucine, leucine, methionine, phenylalanine, proline, tryptophane, tyrosine and valine)

(2) hydrophilic amino acids (arginine, asparagines, aspartic acid, cysteine, glutamic acid, glutamine, glycine, histidine, lysine, serine and threonine); (3) amino acids having aliphatic side-chain (alanine, glycine, isoleucine, leucine, phenylalanine and valine); (4) amino acids having hydroxyl group-containing side-chain (serine, threonine and tyrosine); (5) amino acids having sulfur atom-containing side chain (cysteine and methionine); (6) amino acids having carboxylic acid- and amide-containing side chain-(aspargine, aspartic acid, glutamic acid and glutamine); (7) amino acids having base-containing side chain (arginine, histidine and lysine); and (8) amino acids having aromatic-containing side chain (histidine, phenylalanine, tyrosine and tryptophane).

Examples of proteins or polypeptides having one or more amino acid residues added thereto include, but are not limited to, fusion proteins. For example, to prepare a polynucleotide encoding a fusion protein, a first DNA encoding an angiogenic growth factor and a second DNA encoding another protein or polypeptide are linked in frame. The protein or polypeptide that can be fused to the angiogenic growth factor is not limited to any specific protein or polypeptide.

The activity of a mutant protein can be confirmed according to conventional methods, using well-known assays. For example, the angiogenic activity of mutated proteins and polypeptides of angiogenic growth factors can be confirmed according to a method described in the Examples below, wherein the effect of a protein to induce therapeutic angiogenesis in rat ischemia hindlimb model is detected. Alternatively, the activity of a mutant NOS can be measured according to the method described in WO97/07824, wherein the activity of a protein to induce proliferation of hemangioendothelial cells is detected.

According to the present invention, a gene encoding a first angiogenic growth factor can be used alone or in combination with one or more genes encoding other angiogenic growth factors. Furthermore, genes encoding transcriptional factors regulating the expression of angiogenic growth factors, such as hypoxia-inducible factor (HIF)-1α and Ets-1, can be also used in combination with the gene encoding an angiogenic growth factor in the present invention.

The gene encoding an angiogenic growth factor and other genes used according to needs in combination with the angiogenic growth factor encoding gene in the present invention are preferably inserted into (a) vector(s) which ensures expression of the genes in vivo, and which may be administered to the patient by the "naked" DNA method into lesions or surrounding muscle sites thereof. To express the gene(s), any expression vector may be used, so long as it enables expression of the object gene(s) in vivo. For example, such expression vectors include, but are not limited to, PCAGGS (Gene 108: 193-200 (1991)), PBK-CMV (Stratagene), pcDNA3.1 (Invitrogen), pZeoSV (Invitrogen), etc. The expression vector may further comprise regulatory genes, such as a promoter, enhancer and/or terminator, that are required for the expression of the angiogenic growth factor gene.

The expression vector(s) comprising an angiogenic growth factor gene may be formulated as a pharmaceutical composition suitable for gene therapy by the naked DNA method. For example, for administration by injection, the vector comprising the gene is dissolved in an appropriate solution. Then, the solution comprising the vector is sterilized by filtration according to particular needs and may be filled in an aseptic ampoule and such. According to needs, conventionally used carriers may be added to the solution for injection.

Preferred solutions for dissolving the angiogenic growth factor-encoding gene include, buffer solutions, such as phosphate buffered saline (PBS), physiological saline, sucrose solution, glucose solution, sterilized water, etc. The experimental results reported herein suggest and demonstrate that high transfection efficiency may be achieved by saline as well as PBS. Furthermore, higher transfection efficiency was obtained with the use of glucose solution as compared to sucrose solution. Thus, particularly preferred solutions for the present invention include saline, PBS and glucose solution.

According to the present invention, an angiogenesis-dependent symptom may be treated or prevented in a subject by injecting into a muscle a suitable naked plasmid DNA under a condition wherein the pressure inside the muscle is increased. Increasing "the pressure inside the muscle" means that the pressure on the surface of the cells of the muscle is increased. Such increase in pressure can be achieved by injecting large volumes of solutions, i.e., injecting the naked plasmid DNA dissolved in a solution of a large volume or together with an additional injection of a solution. Alternatively, the additional solution, that without naked plasmid DNA, can be injected after a sufficient time interval from the injection of the naked plasmid DNA, so long as such results in an increase in transfection efficiency.

Furthermore, according to the present invention, the transfection efficiency of a naked plasmid DNA introduced into a subject can be also increased by performing hyperbaric oxygen (HBO) therapy in combination with administration of the naked plasmid DNA. HBO therapy involves exposing a subject to compressed oxygen (more than 1 atm., generally 3 to several atm.). According to the invention, it is preferable to conduct the HBO therapy by exposing the subject to 100% oxygen.

For HBO therapy, a monoplace chamber (adapted for one person) compressed with pure oxygen can be used; alternatively, the subject may be made to breathe oxygen through a mask, headtent (oxygen tent) or endotracheal tube in a multiplace chamber with compressed air. HBO therapy is known to increase the oxygen level in plasma, organs and tissues.

HBO therapy may be performed together with the intramuscular injection of naked plasmid DNA, though it is preferable to start the therapy immediately after the injection.

Although the dosage of the angiogenic growth factor-encoding gene varies depending on the weight, age, sex and symptom of the patient, the kind of gene to be administered, the administration method and so on, one skilled in the art can readily select an appropriate dose of the gene for therapeutic or preventive treatment of angiogenesis-dependent symptoms using routine calculations and well-known algorithms. Generally, the gene is administered to an adult (calculated as a body weight of 60 kg) once every few days or few months at a range of 0.0001 to 100 mg and preferably 0.001 to 10 mg. For administration to other animals, the amount of the gene may be converted for the amount per 60 kg body weight can be administered.

The following examples are presented to illustrate the present invention and to assist one of ordinary skill in making and using the same. The examples are not intended to otherwise limit the scope of the invention in any way.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. Any patents, patent applications and publications cited herein are incorporated by reference.

EXAMPLE 1

General Methods (1) In Vivo Gene Transfer Using Direct Intramuscular Injection Approach Sprague-Dawley rats (400-500 g; Charles River Breeding Laboratories) were anesthetized with an intraperitoneal injection of sodium pentobarbital (0.1 ml/100 mg). Naked luciferase gene (500 µl/animal) or control (500 µg/animal) vector was carefully injected directly into the center of the pretibial muscle of the right hindlimb of rats with a 27 G needle (Terumo, Atsugi, Japan) (Y. Taniyama et al., Gene Ther. 8: 181-189 (2000); M. Aoki et al., Gene Ther. 7: 417-427 (2000); Y. Taniyama et al., Circulation 104: 2344-2350 (2001); R. Morishita et al., Circulation 105: 1491-1496 (2002)). A luciferase gene expression vector driven by SV40 promoter (Promega Corporation, Madison, Wis.) was used as the naked luciferase gene vector.

1) To increase the pressure within the muscle, the manchette of sphygmomanometer was wrapped on the muscle injected with naked luciferase plasmid DNA immediately after transfection.
2) To add pressure at the injection sites, additional intramuscular injection of PBS solution without plasmid DNA was given to the muscle injected with naked luciferase plasmid DNA at 0.5 or 5 hours after transfection.

(2) Analysis of Luciferase Activity

Firefly luciferase activity was measured using luciferase assay system (PicaGene™; Toyo-Inki, Tokyo, Japan). Rats were sacrificed 2 days after transfection of the luciferase gene by direct injection of naked plasmid into the hindlimb. Tissue samples (200 mg around the injection site) were rapidly frozen in liquid nitrogen, and homogenized in lysis buffer. The tissue lysates were briefly centrifuged (3000 rpm, 10 min), and 20 µl of supernatant was mixed with 100 µl of luciferase assay reagents. Measurement of the luminescent reaction was started 5 sec after the addition of sample. Counting lasted for 10 sec, and the count in 10 sec was used as an index of luciferase activity (M. Aoki et al., J. Mol. Cell. Cardiol. 29: 949-959 (1997)).

(3) HBO Therapy ($O_2$ Exposures)

Rats were anesthetized with ketamine (100 mg/kg) and xylazine (5 mg/kg). Intramuscular injection of plasmid DNA was performed as described above. On the morning of exposure, animals were placed in a hyperbaric chamber. The chamber was flushed with 100% $O_2$ for 1.5 min to rise the $O_2$ level to >99%. The animals were exposed to 2 atm 100% $O_2$ for 1 hour, immediately after the transfection.

(4) Statistical Analysis

All values are expressed as mean ±SEM. Analysis of variance with subsequent Duncan's test was used to determine the significance of differences in multiple comparisons. Differences with a P value less than 0.05 were considered significant.

EXAMPLE 2

Comparison of Transfection Efficiency into Rat Muscle In Vivo

Figure 2:
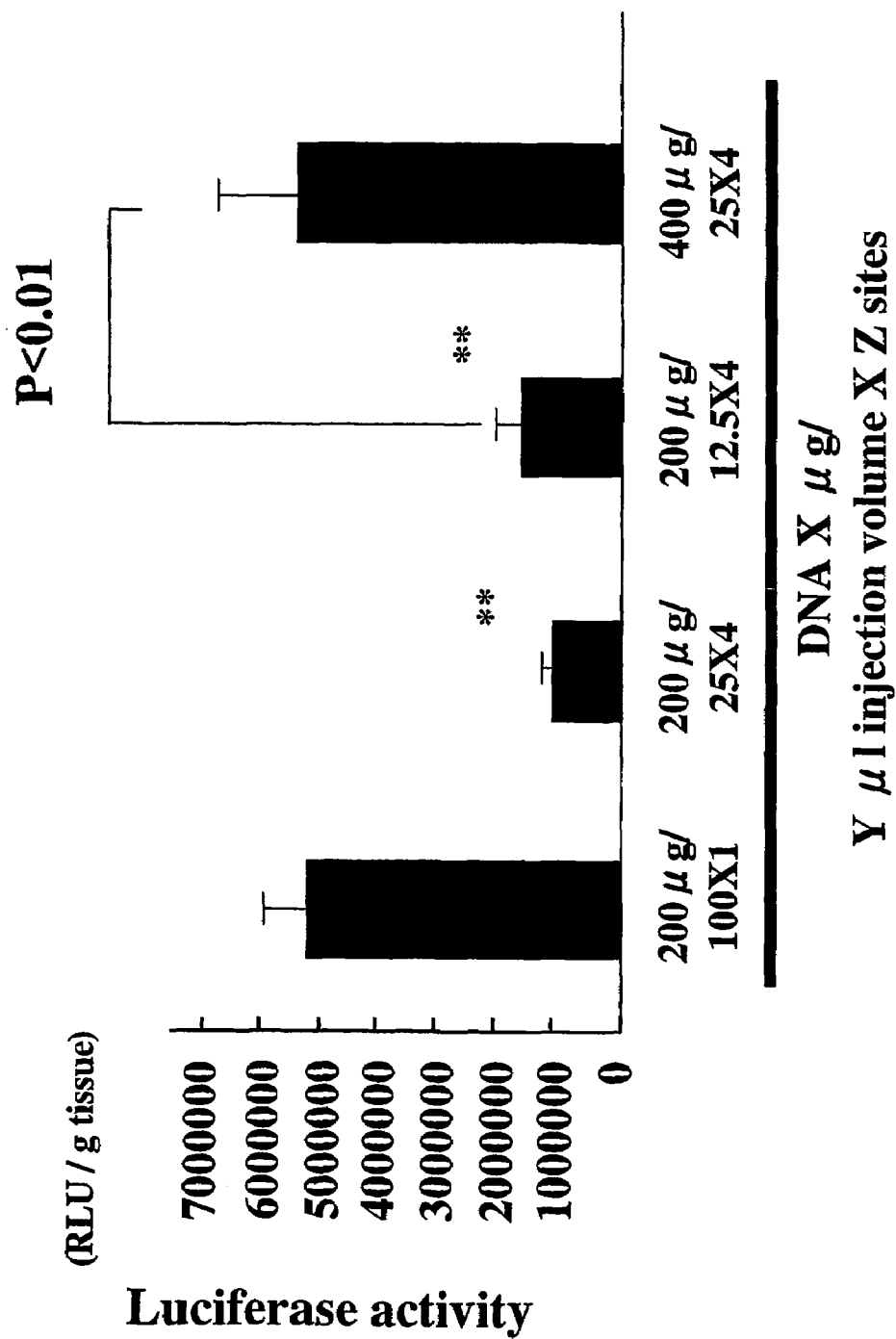
FIG. 2 depicts a graph showing the comparison of luciferase activities detected 2 days after transfection of naked plasmid DNA at various injection volumes and different sites of the skeletal muscle in vivo. 200 ug/100×1: rats transfected with naked luciferase plasmid DNA (200 μg) diluted in 100 μl PBS at one site; 200 ug/25×4: rats transfected with naked luciferase plasmid DNA (200 μg) diluted in 25 μl PBS at 4 sites; 200 ug/12.5×8: rats transfected with naked luciferase plasmid DNA (200 μg) diluted in 12.5 μl PBS at 8 sites; and 400 ug/25×4: rats transfected with naked luciferase plasmid DNA (400 μg) diluted in 25 μl PBS at 4 sites. Each group contained 10 animals. **$p<0.01$ vs. 200 g/100×1.

Initially, we examined the effect of the injection volume on the transfection efficiency of naked plasmid DNA comprising the luciferase gene. As expected, the activity of luciferase increased due to the plasmid DNA in a dose-dependent manner (FIG. 1; $p<0.01$) Interestingly, as shown in FIG. 1, the transfection of naked plasmid DNA increased in relation with the increase in the injection volume of solution (PBS)($p<0.01$). The increase in injection volume (100 µl at one site), rather than separate injections (25 ml at 4 sites or 12.5 ml at 8 sites), gave high transfection efficiency (FIG. 2, $p<0.01$). Thus, the transfection efficiency of naked plasmid DNA seemed to be related to the osmotic pressure.

Figure 3:
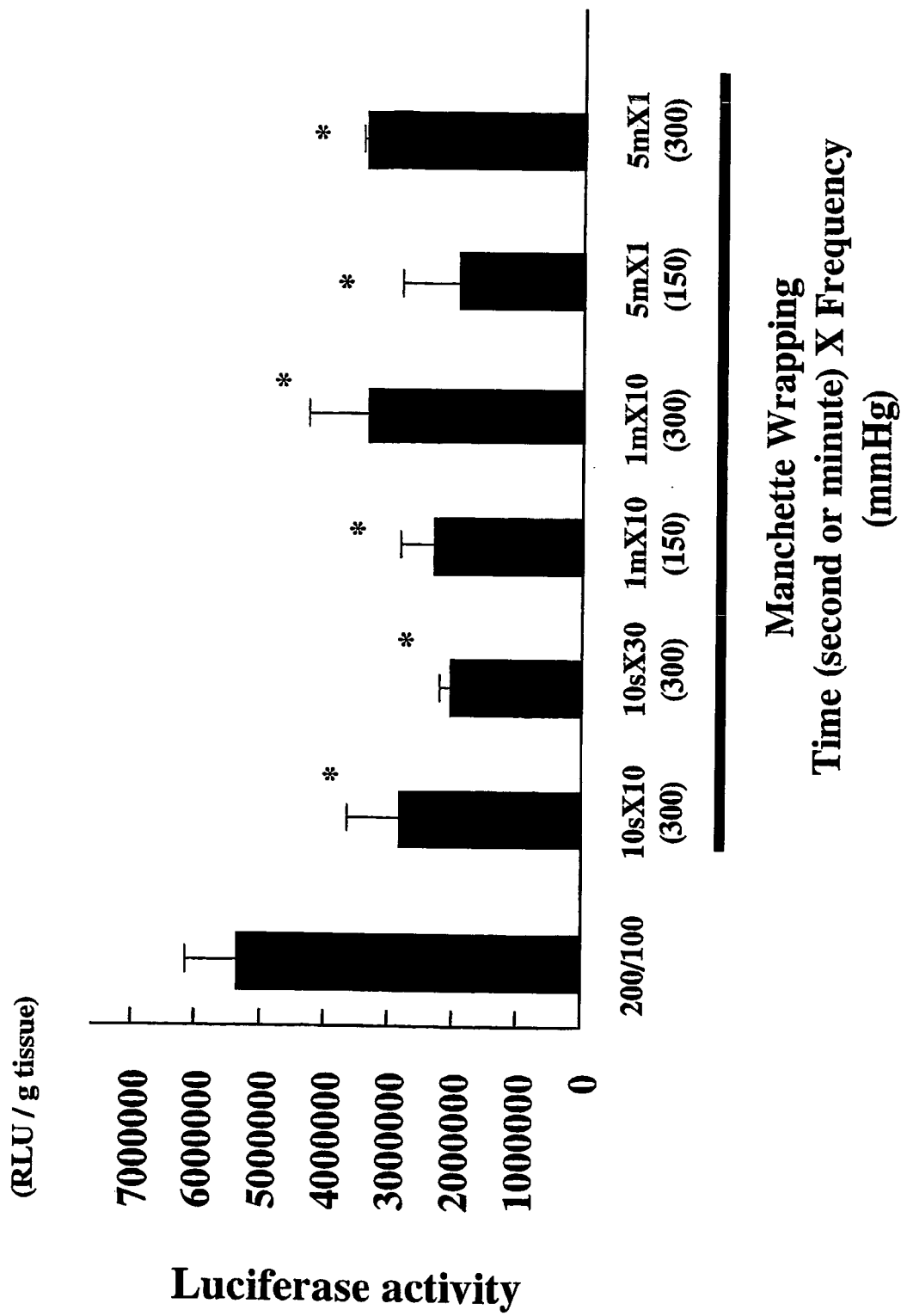
FIG. 3 depicts a graph showing the comparison of luciferase activities detected 2 days after transfection of naked plasmid DNA into the skeletal muscle using manchette wrapping. The manchette of sphygmomanometer was wrapped on the muscle transfected with naked luciferase plasmid DNA immediately after transfection. 200/100: rats transfected with naked luciferase plasmid DNA (200 μg) diluted in 100 μl PBS without manchette wrapping; 10 s/10(300): rats transfected with naked luciferase plasmid DNA (200 μg) diluted in 200 μl PBS compressed 10 times by the manchette for 10 seconds at 300 mmHg; 10 s/30 (300): rats transfected with naked luciferase plasmid DNA (200 μg) diluted in 200 μl PBS compressed 30 times by the manchette for 10 seconds at 300 mmHg; 1 m/10(150): rats transfected with naked luciferase plasmid DNA (200 μg) diluted in 200 μl PBS compressed 10 times by the manchette for 1 minute at 150 mmHg; 1 m/10(300): rats transfected with naked luciferase plasmid DNA (200 μg) diluted in 200 μl PBS compressed 10 times by the cuff for 1 minute at 300 mmHg; 5 m/1(150): rats transfected with naked luciferase plasmid DNA (200 μg) diluted in 200 μl PBS compressed 1 time by the manchette for 5 minutes at 150 mmHg; and 5 m/1(300) rats transfected with naked luciferase plasmid DNA (200 μg) diluted in 200 μl PBS compressed 1 time by the manchette for 5 minutes at 300 mmHg. Each group contained 4 animals. *$p<0.05$ vs. 200/100.

To clarify this hypothesis, the inventors used the manchette of sphygmomanometer on the hindlimb after injection, to increase the pressure from outside. Unexpectedly, neither the manchette-mediated pressures at 150 and 300 mmHg increased the transfection efficiency (FIG. 3). Furthermore, the transfection efficiency was not affected by repeated press of manchette (FIG. 3).

Figure 4A:
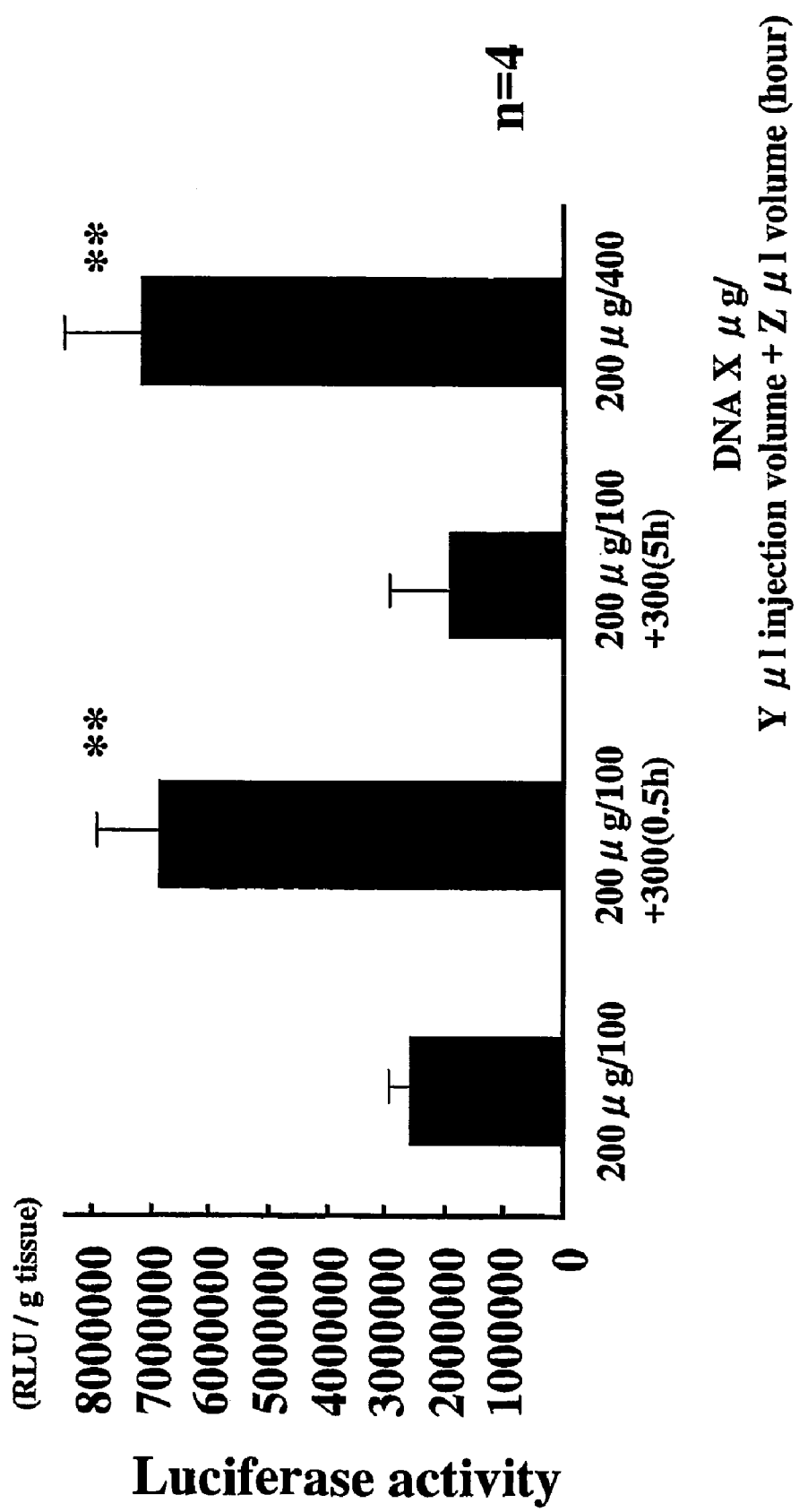
FIG. 4a depicts a graph showing the comparison of luciferase activities detected 2 days after transfection of naked plasmid DNA (200 μg) into the skeletal muscle with additional injection of PBS solution. A PBS solution without plasmid DNA was additionally injected intramuscularly after 0.5 or 5 hours after the transfection of naked luciferase plasmid DNA into the same site of the muscle. 200 ug/100: rats transfected with naked luciferase plasmid DNA (200 μg) diluted in 100 μl PBS; 200 ug/100+300(0.5 h): rats transfected with naked luciferase plasmid DNA (200 μg) diluted in 100 μl PBS followed by injection of 300 μl PBS 30 minutes after the transfection; 200 ug/100+300(5 h): rats transfected with naked luciferase plasmid DNA (200 μg) diluted in 100 μl PBS followed by injection of 300 μl PBS 5 hours after the transfection; and 200 ug/400: rats transfected with naked luciferase plasmid DNA (200 μg) diluted in 400 μl PBS. Each group contained 4 animals. **$p<0.01$ vs. 200 ug/100.
Figure 4B:
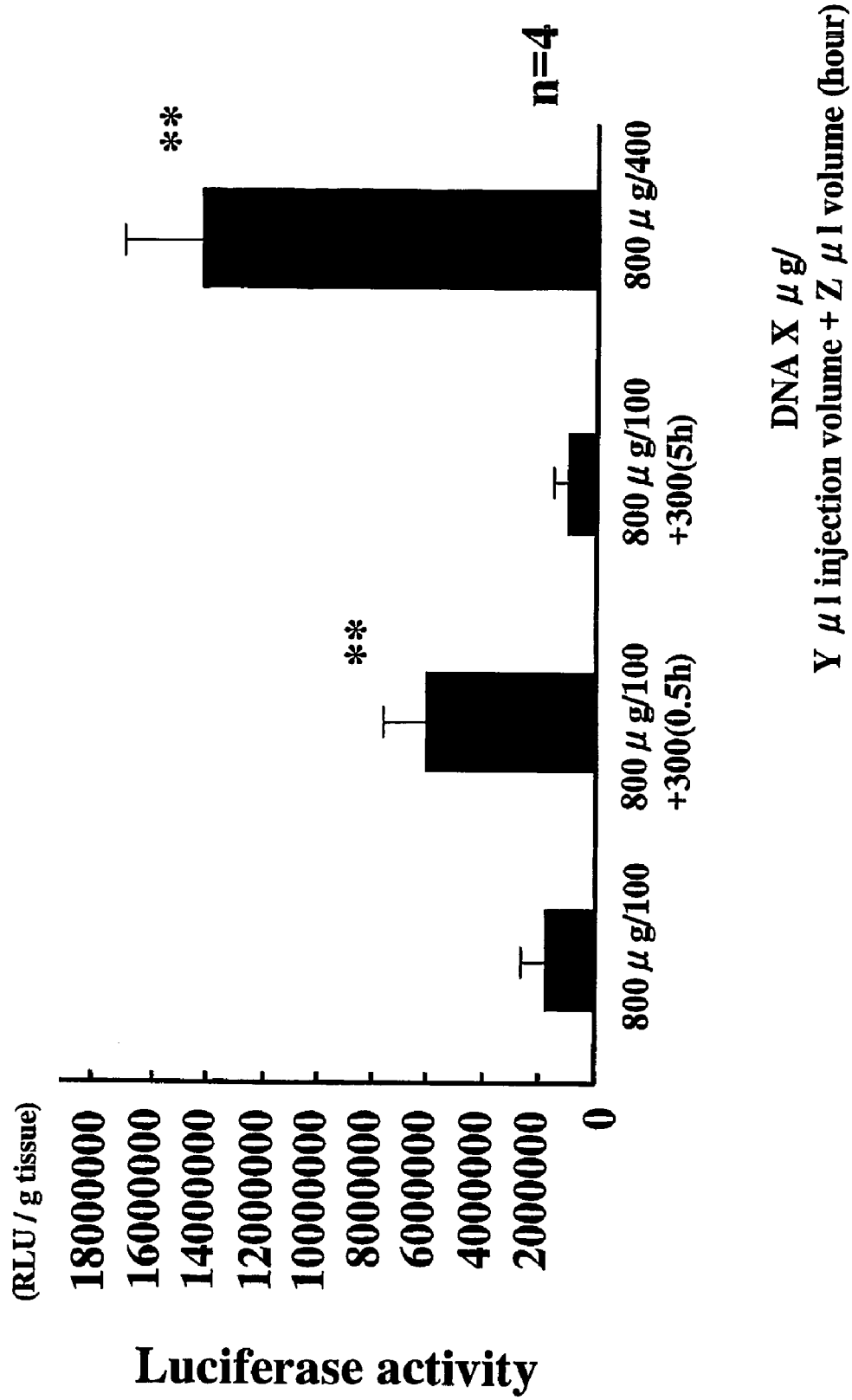
FIG. 4b depicts a graph showing the comparison of luciferase activities detected 2 days after transfection of naked plasmid DNA (800 μg) into the skeletal muscle with additional injection of PBS solution. A PBS solution without plasmid DNA was additionally injected intramuscularly after 0.5 or 5 hours after the transfection of naked luciferase plasmid DNA to into the same site of the muscle. 800 ug/100: rats transfected with naked luciferase plasmid DNA (800 μg) diluted in 100 μl PBS; 800 ug/100+300(0.5 h): rats transfected with naked luciferase plasmid DNA (800 μg) diluted in 100 μl PBS followed by injection of 300 μl PBS alone 30 minutes after the transfection; 800 ug/100+300(5 h): rats transfected with naked luciferase plasmid DNA (800 μg) diluted in 100 μl PBS followed by injection of 300 μl PBS 5 hours after the transfection; and 800 ug/400: rats transfected with naked luciferase plasmid DNA (800 μg) diluted in 400 μl PBS. Each group contained 4 animals. **$p<0.01$ vs. 800 ug/100.

Thus, to increase the inside pressure, PBS without plasmid DNA was intramuscularly injected on the same site of plasmid DNA transfection. As shown in FIG. 4a, additive injection of PBS 30 minutes (0.5 hrs) after the first injection of plasmid DNA increased the luciferase activity ($p<0.011$). Nevertheless, similar additive injection of PBS alone 5 hours after the initial transfection did not increase the luciferase activity. Using 800 µg of plasmid DNA, similar results were obtained (FIG. 4b). In contrast, changes in the injection speed did not affect the transfection efficiency (data not shown).

Figure 5:
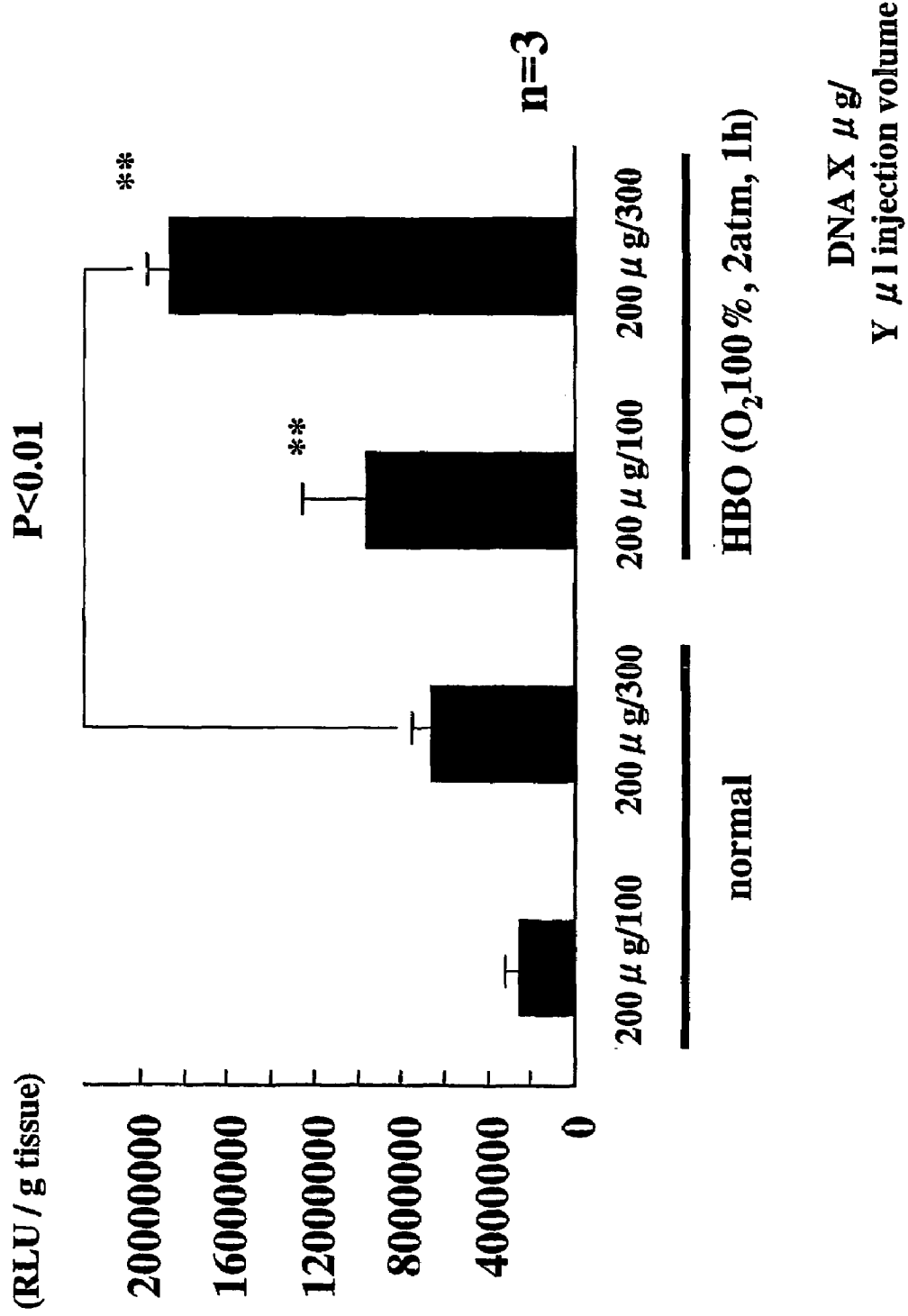
FIG. 5 depicts a graph showing the effect of HBO therapy on luciferase activity 2 days after transfection of naked plasmid DNA (200 μg) into the skeletal muscle. 200 ug/100: rats transfected with naked luciferase plasmid DNA (200 μg) diluted in 100 μl PBS; and 200 ug/300: rats transfected with naked luciferase plasmid DNA (200 μg) diluted in 300 μl PBS. normal: normal condition; HBO: HBO therapy with 100% $O_2$ at 2 atm for 1 hour. Each group contained 3 animals. **$p<0.01$ vs. 200 ug/100.

For further confirmation, HBO therapy was employed. In HBO therapy, animals are exposed to an environment of pure oxygen under high pressure. HBO therapy at 2 atm for 1 hour achieved a significant increase in the luciferase activity in both animals injected with injection volumes of 100 µl and 300 µl (FIG. 5, $p<0.01$). These results demonstrated that the transfection efficiency of intramuscular injection of naked plasmid DNA was dependent on the pressure at the cell surface.

Figure 6A:
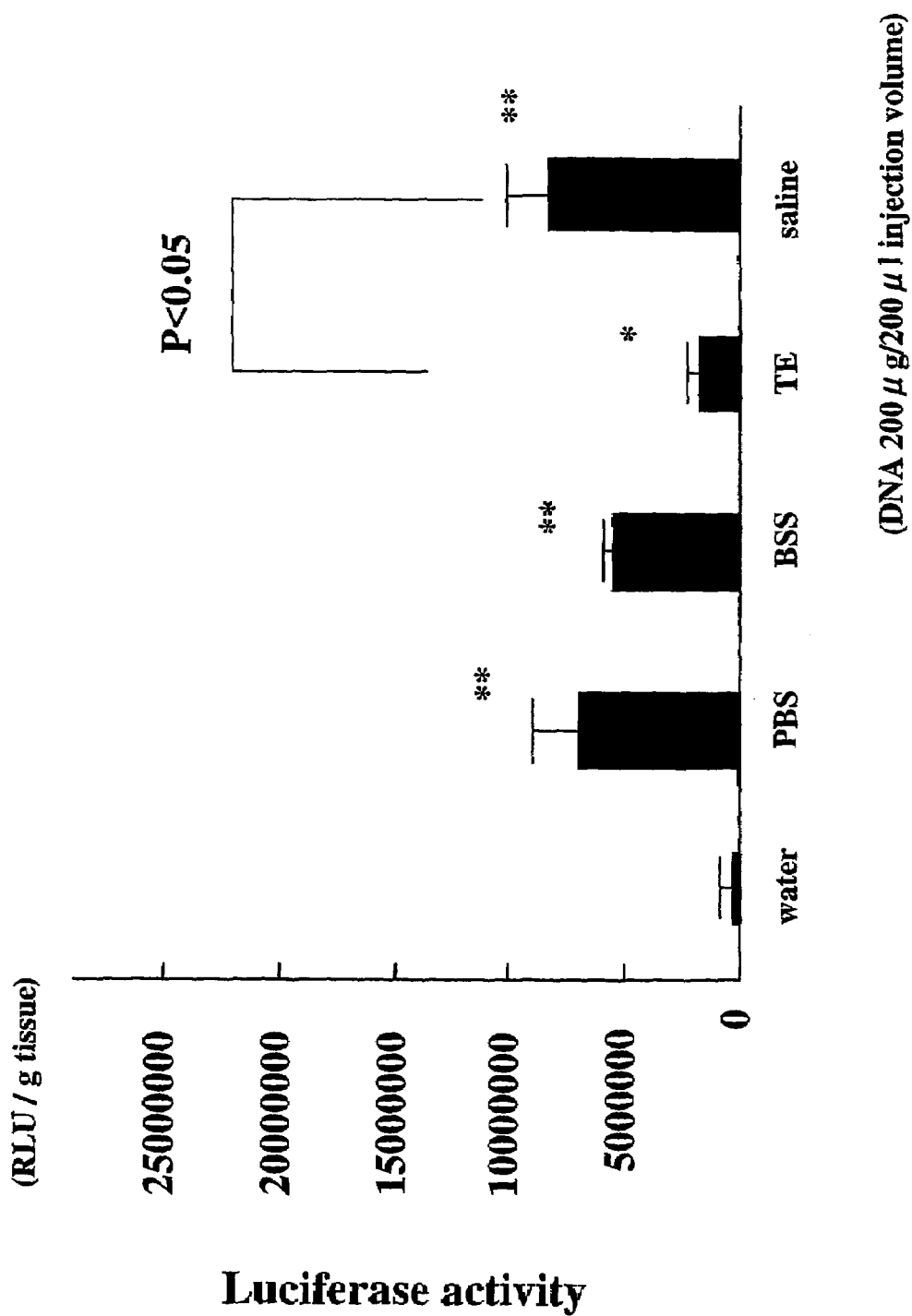
FIG. 6a depicts a graph showing effects of various solutions on the luciferase activity 2 days after the transfection of naked plasmid DNA (200 μg) into the skeletal muscle. Intramuscular injection of luciferase plasmid DNA (200 μg) diluted in various solutions (200 μl injection volume) was performed. PBS: phosphate buffer saline; BSS: balanced saline solution; and TE: Tris-HCl EDTA buffer. Each group contained 6 animals. **$p<0.01$ vs. water.

Alternatively, an increase in osmotic pressure may affect the transfection efficiency. Thus, the influence of the use of various solutions as injection vehicles of plasmid DNAs on transfection efficiency was examined. As shown in FIG. 6a, saline as well as PBS demonstrated high transfection efficiency as compared to other buffers. Unexpectedly, the use of water as the injection vehicle diminished the luciferase activity. To increase osmotic pressure in vivo, glucose and sucrose solutions were also tested for their effect. Both sucrose and glucose solutions increased the expression of luciferase, and sucrose solution rather than glucose solution significantly increased the luciferase activity as compared to water ($p<0.01$). However, the use of a 30% sucrose solution caused injury at the injected site of the muscle thus is not particularly preferred.

INDUSTRIAL APPLICABILITY

The present invention provides modified methods of plasmid DNA-based gene delivery into the skeletal muscle that are safer and achieve higher transfection efficiency as compared to conventional methods. Specifically, the present invention provides a method for treating or preventing diseases by intramuscular injection of suitable naked plasmid DNA under increased pressure inside the muscle. Furthermore, the present method provides a method for treating or preventing diseases by intramuscular injection of suitable naked plasmid DNA in combination with hyperbaric oxygen (HBO) therapy.

According to the present methods, the amount of plasmid DNA to be administered can be decreased and thus the potential cost for naked plasmid DNA therapy can be reduced. Furthermore, these methods achieve efficient transfection without a viral vector, such as adenoviral vectors. In particular, the present methods are more safe as compared to methods utilizing viral vectors and open up the possibility of gene therapy for a wide variety of diseases. Moreover, the combination of naked plasmid DNA administration and HBO therapy of the present invention may expand the utility of angiogenic growth factors in human clinical gene therapy of angiogenesis-dependent conditions, such as wound healing, inflammatory disease, ischemia heart diseases, myocardial infarction and peripheral arterial diseases.

While the invention has been described in detail and with reference to specific embodiments thereof, it will be apparent to one skilled in the art that various changes and modifications can be made therein without departing from the spirit and scope of the invention.

The invention claimed is:

1. A method for treating critical limb ischemia in a subject comprising the step of administering by direct injection a naked plasmid DNA containing a DNA that encodes hepatocyte growth factor (HGF) and that is operably linked to a promoter into the ischemic muscle of an isehemic limb in combination with hyperbaric oxygen (HBO) therapy, wherein the promoter is the simian virus 40 (SV40) promoter or cytomegalovirus (CMV) promoter.

2. The method of claim 1, wherein the HBO therapy is conducted by exposure of 100% oxygen.

3. The method of claim 1, wherein the subject to be treated is subjected to the HBO therapy immediately after the plasmid DNA administration.

4. The method of claim 1, wherein the naked plasmid DNA is diluted in saline, PBS, sucrose solution, or glucose solution.

* * * * *